(12) United States Patent
Reif et al.

(10) Patent No.: US 10,294,447 B2
(45) Date of Patent: May 21, 2019

(54) BIOREACTOR WITH CONDENSER

(75) Inventors: Oscar-Werner Reif, Hanover (DE); Gerid Hellwig, Goettingen (DE); Juergen Van Den Boogaard, Dransfeld (DE); Ute Noack, Goettingen (DE)

(73) Assignee: SARTORIUS STEDIM BIOTECH GMBH, Goettingen (DE)

(*) Notice: Subject to any disclaimer, the term of this patent is extended or adjusted under 35 U.S.C. 154(b) by 1068 days.

(21) Appl. No.: 12/994,270

(22) PCT Filed: May 7, 2009

(86) PCT No.: PCT/EP2009/003255
§ 371 (c)(1),
(2), (4) Date: Nov. 23, 2010

(87) PCT Pub. No.: WO2009/146769
PCT Pub. Date: Dec. 10, 2009

(65) Prior Publication Data
US 2011/0076759 A1 Mar. 31, 2011

(30) Foreign Application Priority Data
May 30, 2008 (DE) .................. 10 2008 025 968

(51) Int. Cl.
*C12M 1/00* (2006.01)
*C12M 1/107* (2006.01)

(52) U.S. Cl.
CPC ........... *C12M 21/04* (2013.01); *C12M 23/14* (2013.01); *C12M 23/28* (2013.01); *C12M 23/36* (2013.01); *C12M 47/18* (2013.01); *C12M 47/20* (2013.01)

(58) Field of Classification Search
CPC .......... C12M 1/12; C12M 1/121; C12M 1/02; C12M 47/18; C12M 21/04; C12M 23/14; C12M 23/28; C12M 23/36; C12M 47/20; B01D 45/00; B01D 53/00; B01D 8/00
USPC ...................................... 435/297.1
See application file for complete search history.

(56) References Cited

U.S. PATENT DOCUMENTS

| 2,067,019 A | 12/1933 | Riegler |
| 2,105,992 A | 12/1933 | Tolman |
| 2,816,064 A * | 12/1957 | Smith .............................. 203/10 |
| 3,063,259 A | 11/1962 | Hankison et al. |
| 4,727,871 A * | 3/1988 | Smargiassi et al. ..... 128/204.17 |
| 5,443,985 A | 8/1995 | Lu et al. |

(Continued)

FOREIGN PATENT DOCUMENTS

| DE | 1601144 | 11/1970 |
| EP | 1 167 905 | 1/2002 |

(Continued)

OTHER PUBLICATIONS

International Preliminary Report.

*Primary Examiner* — Kevin Joyner
*Assistant Examiner* — Holly M Mull
(74) *Attorney, Agent, or Firm* — Gerald E. Hespos; Michael J. Porco; Matthew T. Hespos

(57) ABSTRACT

Bioreactor with a vessel having at least one gas dissipation duct for gas discharge, the orifice of the gas dissipation duct being connected to a hydrophobic sterile filter and to a condenser arranged between them and having condensation surfaces, a turbulence generator for generating a turbulent flow is arranged in the gas dissipation duct in the region of the condenser.

10 Claims, 3 Drawing Sheets

(56) References Cited

U.S. PATENT DOCUMENTS

| | | | |
|---|---|---|---|
| 5,958,763 A * | 9/1999 | Goffe | 435/303.1 |
| 6,122,021 A | 9/2000 | Hirai et al. | |
| 6,133,021 A | 10/2000 | Gu et al. | |
| 2005/0092181 A1* | 5/2005 | Shih et al. | 95/283 |
| 2005/0272146 A1* | 12/2005 | Hodge et al. | 435/289.1 |
| 2006/0033222 A1 | 2/2006 | Godfrey et al. | |
| 2008/0047259 A1* | 2/2008 | Frydman et al. | 60/286 |
| 2008/0068920 A1* | 3/2008 | Galliher et al. | 366/102 |
| 2009/0035856 A1* | 2/2009 | Galliher | C12M 23/14 |
| | | | 435/383 |

FOREIGN PATENT DOCUMENTS

| | | |
|---|---|---|
| GB | 449 621 | 6/1936 |
| WO | 2006/020177 | 2/2006 |

\* cited by examiner

BIOREACTOR WITH CONDENSER

BACKGROUND OF THE INVENTION

1. Field of the Invention

The invention relates to a bioreactor with a vessel having at least one gas dissipation duct for gas discharge, the orifice of the gas dissipation duct being connected to a sterile filter and to a condenser arranged between them and having condensation surfaces. The invention relates, furthermore, to a condenser for a bioreactor.

2. Description of the Related Art

In the gassing of a bioreactor, the air supplied absorbs moisture while the medium flows through. The same effect occurs in biotechnological processes in which gases are formed as metabolic products of microorganisms and are dissipated out of the bioreactor. Using an outflow condenser in the outflow system makes it possible to prevent the exhaust air from carrying some of the medium out with it. Warm, moist exhaust air is cooled down by the condenser to such an extent that the medium contained in the exhaust air flows as condensate back into the boiler.

U.S. Pat. No. 5,443,985 A discloses a bioreactor with a vessel composed of a borosilicate glass or of stainless steel, which at its vertically upper end has a gas dissipation duct for gas discharge. In this case, the orifice of the gas dissipation duct is closed by means of a sterile filter. A water-cooled condenser is arranged between the vessel and the sterile filter, parts of the inner surfaces of the gas dissipation duct forming the condensation surfaces required in the condenser. The vessel of the known bioreactor is supplied at its vertically lower end with gas via a gas routing duct.

In the known bioreactor, the inner wall surrounding the gas dissipation duct forms the condensation surface of the condenser. The condenser has a double wall, through which the cooling water is led.

The disadvantage, here, is that, in the case of a largely laminar flow, a relative long gas dissipation duct is required in order to cool the entire exhaust air stream sufficiently. Particularly when a bioreactor is used as a disposable reactor with a condenser, it is difficult to achieve a compact form of construction. What proves to be especially critical in this case is the possible blocking of the hydrophobic sterile filter if the vessel of the bioreactor is designed as a flexible plastic bag, the internal pressure of which should not exceed specific limit values so that, if necessary, gassing and therefore the fermentation process have to be discontinued.

Furthermore, U.S. Pat. No. 6,133,021 A discloses a bioreactor, the gas dissipation duct of which is connected to a condenser. This condenser, too, has the disadvantages described above.

Furthermore, DD 260 837 A3 discloses a bioreactor with a vessel which has a gas dissipation duct for gas discharge. The orifice of the gas dissipation duct is connected to an exhaust air filter, a condenser being arranged between the vessel and the exhaust air filter.

This known bioreactor, too, has the abovementioned disadvantages.

EP 1 167 905 A2 discloses an apparatus for removal of volatile components from a gas stream, using a cryogenic process. In order to remove the volatile components from a process gas stream, the gas stream is cooled in a condenser in order to convert the volatile components into liquid and ice. The process gas, which is freed from the volatile components and may still contain ice particles of volatile components, passes through a filter which is arranged downstream of the condenser, in order to remove the ice particles which have a size of more than 50 µm.

This technical application, because of its refrigeration process, is not suitable for or cannot be transferred to bioreactors. The vortex, used in EP 1 167 905 A2, of liquid cryogen for cooling, on the one hand, is unsuitable for bioreactors and, on the other hand, is used in order to generate relatively large ice crystals.

GB 449 621 A discloses an apparatus for the recovery of phthalic anhydride (PSA) from vapors, in which the vapors are routed as a turbulent stream through a tubular condenser. A person skilled in the art is not given any suggestion for the development of bioreactors.

U.S. Pat. No. 3,063,259 A discloses an apparatus for the filtration and dehydration of gases. In the condenser known from U.S. Pat. No. 3,063,259 A, the process gas is conducted spirally around a spirally designed cooling wall. There is no question here of a turbulent flow in the gas dissipation duct. Not even this gives a person skilled in the art any suggestion for the development of bioreactors.

WO 2006/020177 A1 discloses a photobioreactor for photosynthetic organisms, such as algae. WO 2006/020177 A1 teaches that, in specific embodiments, a filter, such as, for example, a hydrophobic filter with a main pore diameter smaller than the mean diameter of the algae, can be used in order to prevent the escape of algae from the gas outlet of the bioreactor. Algae filters of this type are not sterile filters.

The object of the present invention, therefore, is to improve the known bioreactors and their condensers such that, while having a compact form of construction, they can be produced from plastic, in particular for disposable use.

SUMMARY OF THE INVENTION

The object is achieved by a bioreactor with a vessel having at least one gas dissipation duct for gas discharge. The orifice of the gas dissipation duct is connected to a condenser arranged between them and having condensation surfaces. The bioreactor is characterized in that the sterile filter is designed as a hydrophobic filter, in that turbulence generation means generating a turbulent flow are arranged in the gas dissipation duct in the region of the condenser, and in that the vessel, the condenser and the sterile filter are produced from gamma-sterilizable plastic.

Arranging turbulence generation means in the gas dissipation duct ensures that the dissipated gas or the exhaust air is routed past the condensation surfaces of the condenser. This allows more efficient heat exchange between the dissipated gas and the coolant of the condenser. The more efficient heat exchange makes it possible, in spite of the use of plastic, to have a more compact type of construction. Designing the sterile filter as a hydrophobic sterile filter is also conducive to a compact type of construction. Producing the vessel, the condenser and the sterile filter from gamma-sterilizable plastic is especially advantageous for delivering ready-to-use presterilized bioreactor systems to customers.

According to a preferred embodiment of the invention, the outer surfaces of the turbulence generation means are designed as condensation surfaces. For example, the turbulence generation means may be designed as a condenser hose or condenser tube which is arranged helically in the gas dissipation duct and through which a cooling liquid can be conducted.

According to a further preferred embodiment of the invention, the inner wall surrounding the gas dissipation duct forms the condensation surface, an outer wall being arranged at a distance from the inner wall, and a cooling liquid being conducted through the interspace between the outer wall and inner wall. The turbulence generation means is in this case designed as a packing which, for example, is produced from a nonwoven material.

According to a further embodiment of the invention, the packing is produced from tubular segments, what are known as Raschig rings. The tubular segments may in this case be produced from glass, ceramic, plastic or metal.

According to a further preferred embodiment of the invention, the sterile filter has on its circumference heating which makes it possible to control the temperature of the exhaust air, with the result that blockage of the hydrophobic filters by condensed liquids is avoided.

According to a further preferred embodiment of the invention, the sterile filter is integrated into the condenser or its housing. This makes it possible to have an especially compact type of construction.

The entire bioreactor, composed of the vessel, of the condenser and of the sterile filter, is designed, according to a further embodiment, as a disposable apparatus. Preferably, in this case, the vessel is designed as a flexible bag.

The object with regard to a condenser is achieved in that turbulence generation means for generating a turbulent flow are arranged in the gas dissipation duct in the region of the condenser.

The condenser has the advantages outlined above.

According to a preferred embodiment of the invention, the turbulence generation means is designed as a condenser hose or condenser tube which is arranged helically in the gas dissipation duct and through which a cooling liquid can be conducted.

In a further preferred embodiment of the invention, the condenser hose is surrounded by further combined cooling and turbulence generation means, such as nonwoven material or formed thin individual pieces, preferably made from plastic. In addition to generating turbulence, these means act, on account of their position or their contact with the condenser hose, as cooling surfaces and dispel heat via heat bridges.

According to a further preferred embodiment of the invention, the inner wall surrounding the gas dissipation duct forms the condensation surface, an outer wall being arranged at a distance from the inner wall, and a cooling liquid being capable of being conducted through the interspace between the outer wall and inner wall.

The turbulence generation means may in this case be designed as a packing produced from a nonwoven material or from tubular segments made from glass, ceramic, plastic or metal.

Further features of the invention may be gathered from the following detailed description and the accompanying drawings, in which preferred embodiments of the invention are illustrated by way of example.

DETAILED DESCRIPTION OF THE PREFERRED EMBODIMENTS

Figure 1:
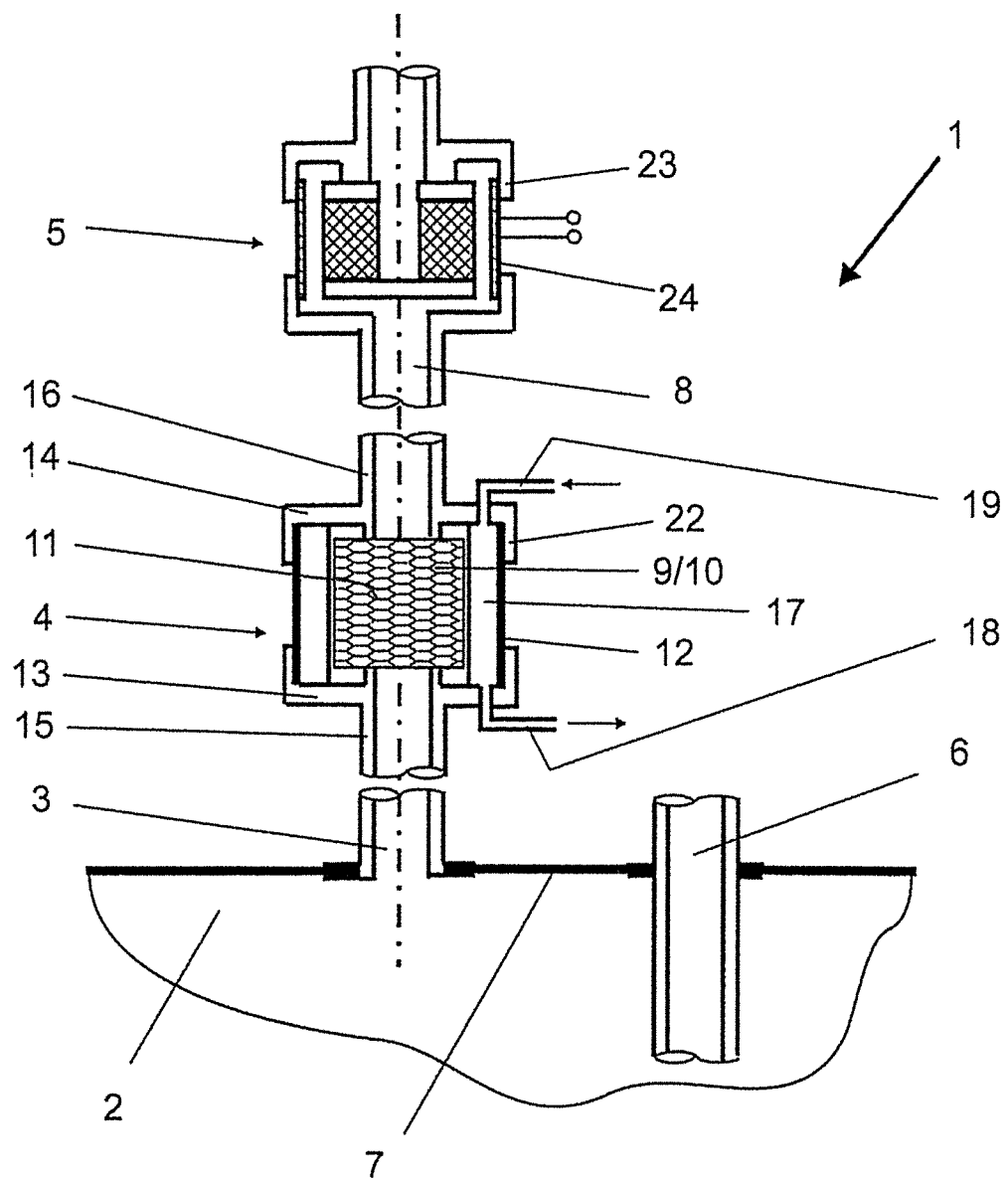
FIG. 1 shows a side view of a bioreactor with a vessel, condenser and sterile filter in section and in elevation.

A bioreactor 1 is composed essentially of a vessel 2, of a gas dissipation duct 3, of a condenser 4, of a sterile filter 5 and of a gas supply duct 6.

The vessel 2 is designed as a bag made from plastic with a flexible wall 7 and has, inter alia, in addition to the gas dissipation duct 3, the gas supply duct 6.

The orifice 8 of the gas dissipation duct 3 is connected to the hydrophobic sterile filter 5. The condenser 4 is arranged in the gas dissipation duct 3 between the vessel 2 and sterile filter 5.

Turbulence generation means 9 for generating a turbulent flow are arranged in the gas dissipation duct 3 in the region of the condenser 4.

Figure 2:
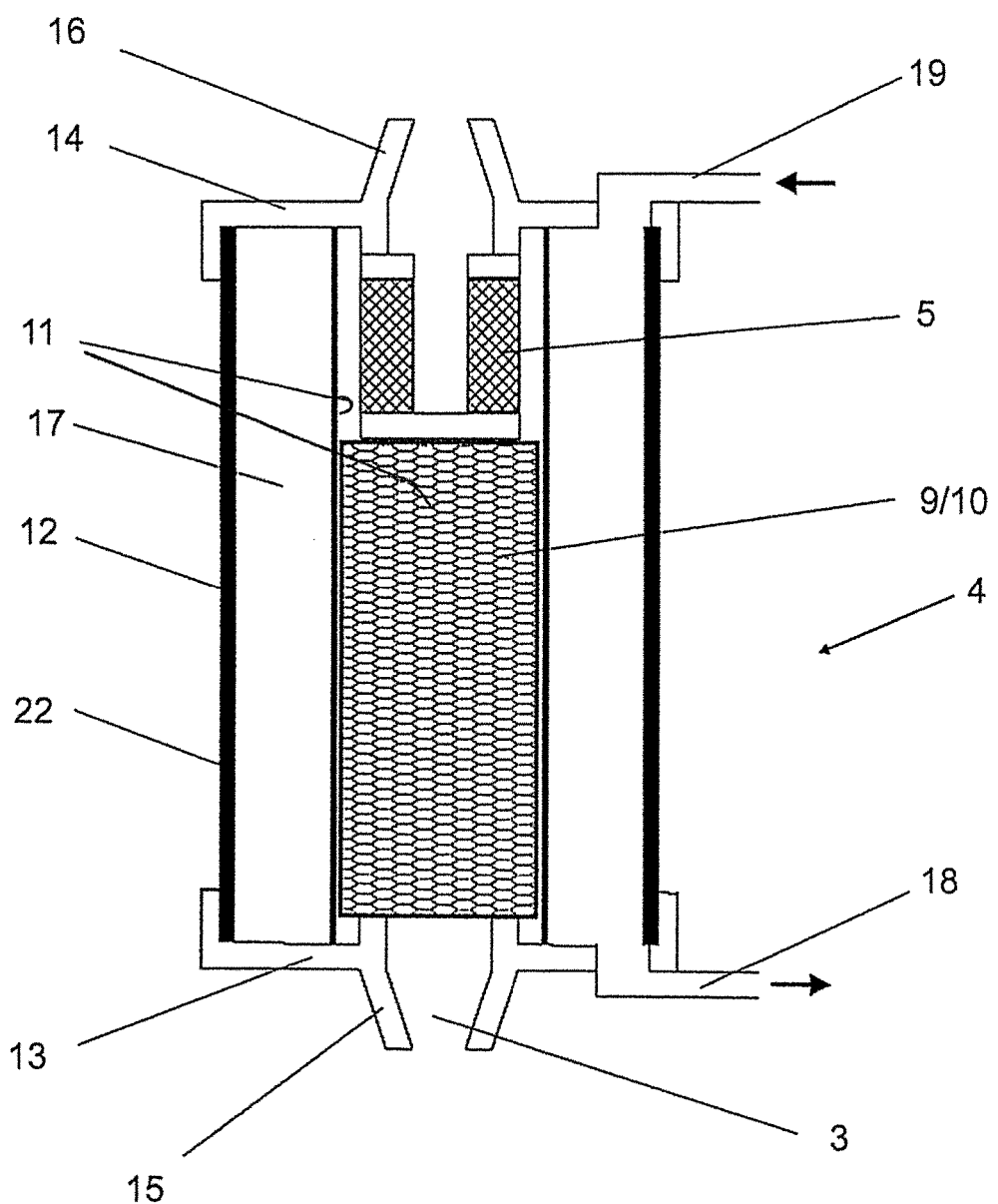
FIG. 2 shows a sectional side view of a condenser with an integrated sterile filter.

According to the exemplary embodiment of FIG. 1 and FIG. 2, the turbulence generation means 9 are designed as a packing 10 inserted into the gas dissipation duct 3 and composed of a nonwoven material or of tubular segments made from glass, ceramic, plastic or metal, and the wall 11 surrounding the gas dissipation duct 3 is formed by an inner tube made from plastic, preferably from polycarbonate, polyethylene or polypropylene. The condenser 4 has, at a distance from the inner wall 11, an outer wall 12 which is formed by an outer tube made from polypropylene. The condenser 4 has on each of its faces a cover 13, 14 with a connection 15, 16 for the gas dissipation duct 3. Coolants are fed into the interspace 17 formed by the walls 11, 12 via an upper coolant connection 19 and are dissipated therefrom via a lower coolant connection 18.

The condensation surface of the condenser 4 is formed by the inner wall 11 according to the exemplary embodiments of FIGS. 1 and 2.

Figure 3:
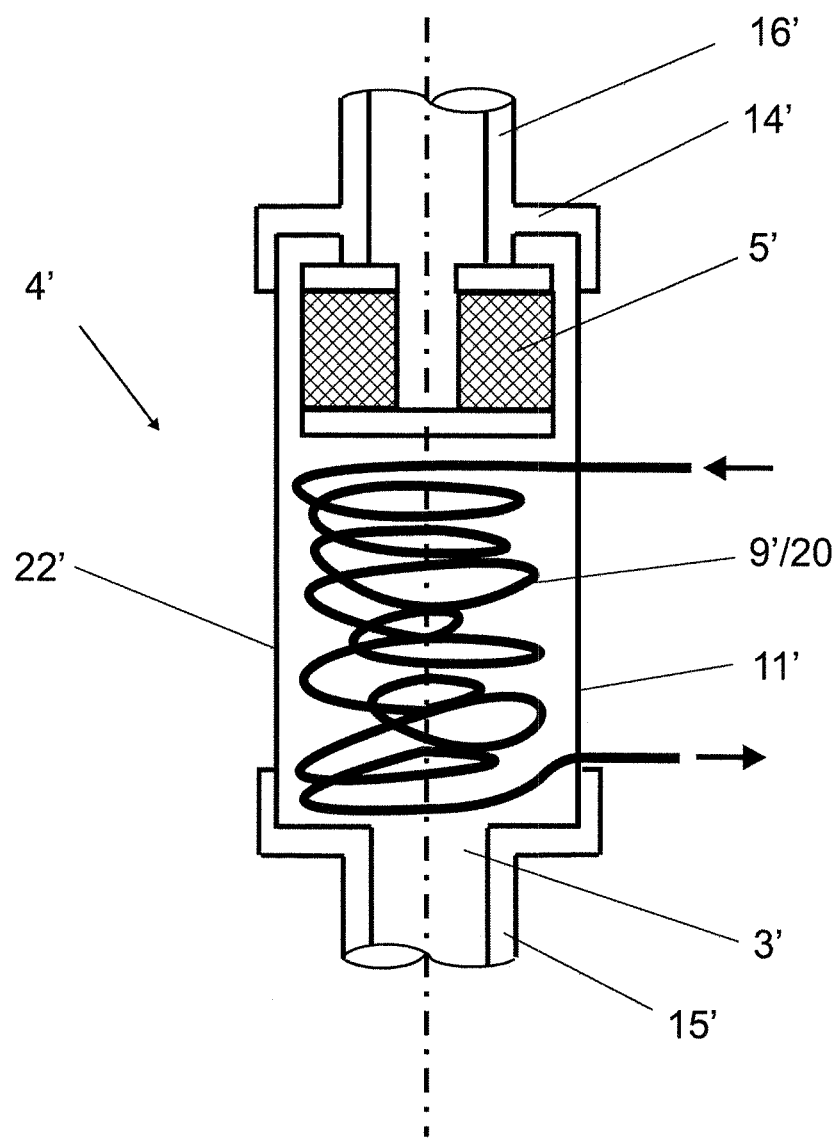
FIG. 3 shows a sectional side view of a condenser.

According to the exemplary embodiment of FIG. 3, the condenser 4' has an inner wall 11' of the gas dissipation duct 3', said inner wall being formed by a tube made from plastic which at the same time forms the outer wall. The turbulence generation means 9' arranged in the gas dissipation duct 3' is formed by a condenser hose 20 which is arranged helically and through which coolant is supplied via its upper connection 16' and is dissipated via its lower connection 15'. In this case, the outer surface 21 of its condenser hose 20 forms the condensation surface of the condenser 4'. The condenser hose 20 may likewise be produced from plastic.

The condenser hose 20 may be surrounded by further combined cooling and turbulence generation means 9, not illustrated, such as nonwoven material or formed thin individual pieces preferably made from plastic.

According to the exemplary embodiments of FIGS. 2 and 3, the sterile filter 5 is integrated into the housing 22, 22' of the condenser 4, 4'. The sterile filter 5, 5' is welded here in each case to the upper cover 14, 14'.

According to the exemplary embodiment of FIG. 1, the hydrophobic sterile filter 5 has, on its circumference or housing 23, heating 24 for controlling the temperature of the gas to be dissipated.

The invention claimed is:
1. A bioreactor (1) comprising: a vessel (2) with a flexible wall (7); a gas dissipation duct (3, 3') joined to the flexible wall (7) and extending up from an upper part of the vessel (2) for gas discharge from the vessel (2), the gas dissipation duct (3, 3') having an orifice (8); a hydrophobic sterile filter (5, 5') connected to the orifice (8) of the gas dissipation duct (3, 3'); and a condenser (4, 4') arranged above the vessel (2) and between the vessel (2) and the hydrophobic sterile filter (5, 5') so that the gas dissipation duct (3, 3') passes through the condenser (4, 4'), an outer wall (12) arranged at a distance out from the gas dissipation duct (3, 3') at the condenser (4, 4') and defining an interspace (17) between the outer wall (12) and the gas dissipation duct (3, 3'), connections (18, 19) communicating with the interspace (17) for conducting coolant through the interspace (17), surfaces of the gas dissipation duct (3, 3') in the condenser (4, 4') being configured to define turbulence generation means (9, 9') for generating a turbulent flow and condensation in the gas dissipation duct (3, 3') inward of the interspace (17), wherein the surfaces of the gas dissipation duct (3, 3') that form the turbulence generation means are above the vessel (2) and communicate gravitationally with the vessel (2) via the gas dissipation duct (3, 3') so that condensate produced at the condenser (4, 4') flows gravitationally down through the gas dissipation duct (3, 3') to the vessel (2), and the vessel (2), the condenser (4, 4') and the sterile filter (5, 5') being integrally connected and produced from gamma-sterilizable plastic and wherein the vessel (2), the condenser (4, 4') and the sterile filter (5, 5') are components of a disposable apparatus.

2. The bioreactor of claim 1, wherein the turbulence generation means (9, 9') is a condenser hose (20) or condenser tube that is arranged helically in the gas dissipation duct (3, 3') and through which a cooling liquid can be conducted.

3. The bioreactor of claim 2, wherein the condenser hose (20) or the condenser tube is surrounded by further combined cooling and turbulence generation means.

4. The bioreactor of claim 1, wherein the turbulence generation means (9, 9') comprises a packing (10).

5. The bioreactor of claim 4, wherein the packing (10) is produced from a nonwoven material.

6. The bioreactor of claim 4, wherein the packing (10) is produced from tubular segments made from glass, ceramic, plastic or metal.

7. The bioreactor of claim 1, further comprising a heating member (24) on an outer circumference of the hydrophobic sterile filter (5, 5').

8. The bioreactor of claim 1, wherein the hydrophobic sterile filter (5, 5') is integrated into the condenser (4, 4').

9. The bioreactor of claim 1, further comprising lower and upper walls (13, 14) connected to opposite upper and lower ends of the outer wall (12) and closing the interspace (17), the upper wall (14) being welded to the sterile filter (5, 5') so that the sterile filter (5, 5') is between the lower and upper walls (13, 14) and inward of the outer wall (12), and with the turbulence generation means (9, 9') being between the sterile filter (5, 5') and the lower wall (13).

10. The bioreactor of claim 9, wherein the turbulence generation means (9, 9') comprises a packing (10) inward of the inner wall (11).

* * * * *